United States Patent [19]
Ceresko

[11] Patent Number: 5,865,372
[45] Date of Patent: Feb. 2, 1999

[54] AIR FRESHENER FOR VEHICLE

[75] Inventor: Joseph P. Ceresko, Mt. Cobb, Pa.

[73] Assignee: Space Age Plastics, Mt. Cobb, Pa.

[21] Appl. No.: 876,186

[22] Filed: Jun. 18, 1997

[51] Int. Cl.⁶ ................................................... A24F 25/00
[52] U.S. Cl. .................................................................. 239/60
[58] Field of Search ................................... 234/34, 60, 57;
422/123, 124, 305, 5

[56] References Cited

U.S. PATENT DOCUMENTS

| | | | |
|---|---|---|---|
| 647,130 | 4/1900 | Bengue | 422/123 |
| 1,178,575 | 6/1996 | Collins | 239/34 |
| 4,285,905 | 8/1981 | Feit | 239/60 |
| 4,808,347 | 2/1989 | Dawn | 239/57 |
| 5,115,976 | 5/1992 | Weiss et al. | 239/60 |
| 5,368,822 | 11/1994 | McNeil | 239/60 |

*Primary Examiner*—Kevin Weldon
*Attorney, Agent, or Firm*—Kane, Dalsimer, Sullivan, Kurucz, Levy, Eisele and Richard, LLP

[57] ABSTRACT

A sphere with undulations, serving as vanes, is pivotally mounted on a stand which has means for clipping the stand to an air vent in an automobile. The sphere has molded therein a fragrance which will be time released when exposed to heat or air currents.

7 Claims, 1 Drawing Sheet

AIR FRESHENER FOR VEHICLE

BACKGROUND OF THE INVENTION

Many passengers travelling in vehicles have experienced from time-to-time either stagnant, musty or even foul air within the cab or interior of the vehicle. This is especially exacerbated when weather conditions do not permit the windows of the vehicle to be opened, as for example when the ambient is extremely cold or stormy. When vehicular travel is extremely prolonged or the smell of smoke, food or other obnoxious odors contribute to the uncomfortable environment, conditions within the vehicle become increasingly unpleasant and unbearable.

Many forms of vaporizers and air fresheners have been proposed to remedy these conditions. As a whole, most have not been entirely satisfactory or efficient.

SUMMARY OF THE INVENTION

A principal object of the present invention is to provide an air freshener for the interior of a vehicle that effectively solves the foregoing problems of the prior art.

Another object is to provide an air freshener of the foregoing type that is cost effective, readily mounted in convenient locations within a vehicle, and, after use, is readily disposable.

A further object is to provide an air freshener of the foregoing type that is aesthetically acceptable and capable of being rendered more efficient by being readily mounted so as to be exposed to air currents within the vehicle.

Other objects and advantages will become apparent from the following detailed description which is to be taken in conjunction with the accompanying drawings.

DETAILED DESCRIPTION

Figure 1:
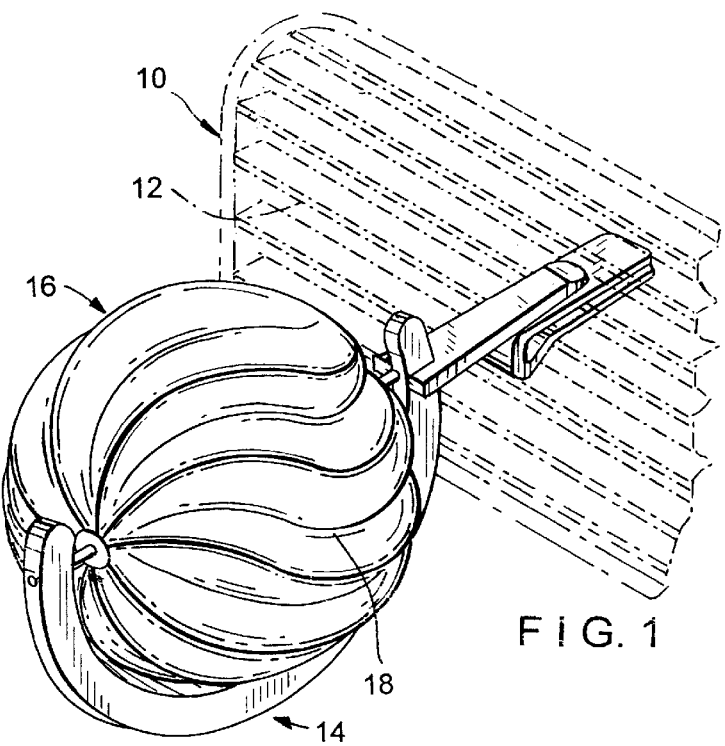
FIG. 1 is a fragmentary perspective view of a vehicle interior showing the air freshener of the present invention mounted on an output air vent of the heating/cooling system.
Figure 2:
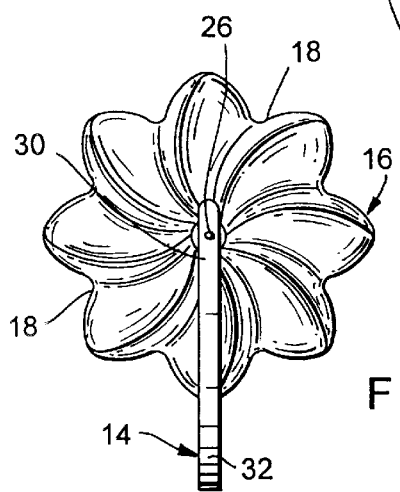
FIG. 2 is a side elevational view of the air freshener.
Figures 3, 4:
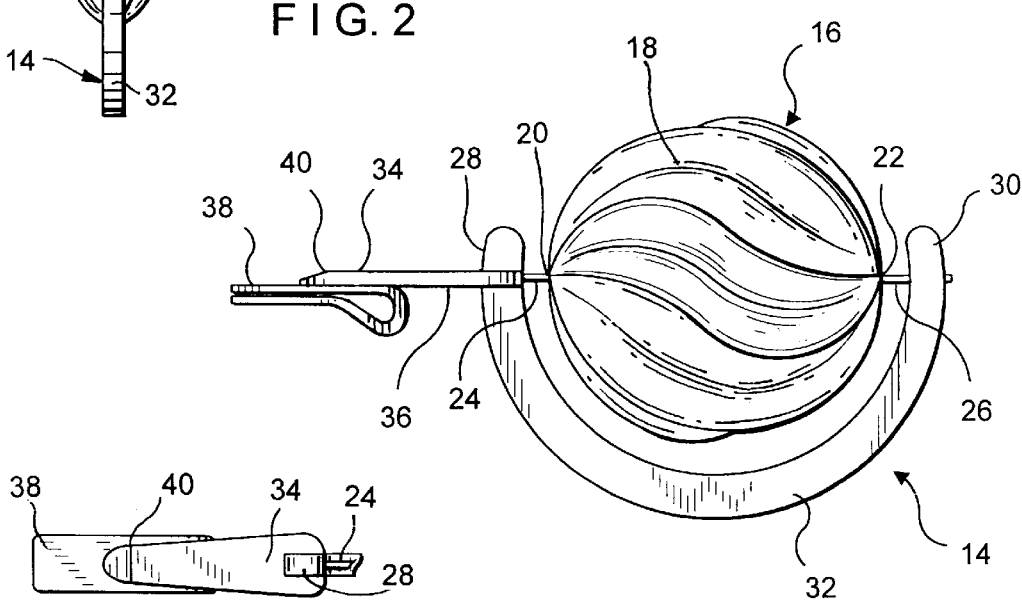
FIG. 3 is a top plain view thereof.
FIG. 4 is an end view thereof.

In the drawings, the interior of a typical vehicle 10 is illustrated together with one of a series of internal vents 12 of the vehicle heating/cooling system. The air freshener 14 of this invention is conveniently mounted on one of the vanes of the vent 12 to take advantage of the air currents normally flowing therethrough. The air freshener 14 includes a slow release generator or reservoir 16 in substantially spherical or ball form. However, as well be apparent, generator 16 may assume many other forms that would be conducive to rotation by air currents. Towards this end, the exterior of the generator 16 may be formed with undulations 18 serving as vanes to enhance the rotation of the generator 16 by the air currents.

In order to facilitate the rotation of the generator 16, diametrically opposed recesses 20,22 in the generator 16 receive pivot pins 24,26 journalled for rotation therein. Pins 24,26 may be metal or other suitable material and extend inwardly from the free ends 28,30 of a semi-circular arm 32 which may be molded of a suitable resin. Arm 32 forms part of a supporting stand for generator 16 and which also includes a leg 34 fixed at one end 36 to the arm 32. A clip 38 extends away from and is fixed to the free end 40 of leg 34. Leg 34 and clip 38 may also be molded of a suitable resin.

The generator 16 is molded of a suitable resin carrier that permits slow release of a volatile compound for freshening the air in the vehicle cab. This volatile compound may be a perfume, fragrance, scent or deodorant to provide the desired aroma or effect within the vehicle. The volatile compound is time-released when exposed to air and/or heat.

In accordance with a successful application of the present invention a matrix of polyethylene pellets is heated in, for example, a single screw extruder and a selected scent or aroma is added to the polymer which is in liquid form. At that point the scent is introduced via high pressure dosing pumps. After the extruder properly mixes the fragrance and polymer, the resultant polymer melt is pelletized and cooled. While the resin is still in liquid form a suitable colorant may be added.

The cooled pellets are considered polymer fragrance masterbatch or concentrates. These pellets with fragrance may then be suitably molded into the configuration of the generator 16 which will be a slow release generator in that it is capable of slowly emitting vapor into the ambient or surrounding atmosphere. The slow release is enhanced by heat and air, as for example, that which emanates from the vehicle vent 12. In this regard, the air freshener 14 may be clipped on a vane of the vent 12 and disposed either vertically or horizontally. Further, the air freshener may be suitably clipped to other parts of the vehicle interior that will be exposed to air currents from the vehicular heating/cooling system or that flowing through an open window to enhance the slow diffusion of the volatile compound with the generator 16.

Thus, the several aforenoted objects and advantages are most effectively attained. Although a single somewhat preferred embodiment of the invention has been disclosed and described in detail herein, its scope is in no sense limited thereby but is to be determined by that of the appended claims.

I claim:

1. An air freshener for mounting in the interior of a vehicle comprising a slow release generator, the generator being molded of a resin containing a volatile compound, a stand, means for rotatable mounting the generator on the stand so that the diffusion of the volatile compound in the vehicle is enhanced by heat and air currents in the vehicle means forming part of the generator for inducing rotation of the generator when exposed to heat and air currents in the vehicle, and means for attaching the stand to an internal surface of the vehicle.

2. An air freshener in accordance with claim 1 wherein the volatile compound is selected from the group consisting of a perfume, fragrance, scent and deodorant.

3. An air freshener for mounting in the interior of a vehicle comprising a slow release generator the generator being molded of a resin containing a volatile compound a stand means for rotatable mounting the generator on the stand so that the diffusion of the volatile compound in the vehicle is enhanced by heat and air currents in the vehicle, the generator having an exterior and is substantially spherical and is formed with undulations on the exterior thereof serving as vanes for inducing rotation of the sphere when exposed to heat and air currents in the vehicle.

4. An air freshener for mounting in the interior of a vehicle comprising a slow release generator the generator being molded of a resin containing a volatile compound. a stand, means for rotatable mounting the generator on the stand so that the diffusion of the volatile compound in the vehicle is enhanced by heat and air currents in the vehicle. wherein the stand including a semi-circular arm having opposed free ends and the generator being journalled for rotation on the opposed free ends of the arm.

5. An air freshener for mounting in the interior of a vehicle comprising a slow release generator, the generator being molded of a resin containing a volatile compound, a stand, means for rotatable mounting the generator on the stand so that the diffusion of the volatile compound in the vehicle is enhanced by heat and air currents in the vehicle, the stand having a leg having a free end and is attached to one of the free ends of the arm and clip means attached to the free end of the leg for attaching the air freshener to an internal surface of the vehicle.

6. An air freshener in accordance with claim 5 wherein the generator has an exterior and is substantially spherical and is formed with undulations on the exterior therein serving as vanes for inducing rotation of the sphere when exposed to heat and air currents in the vehicle.

7. An air freshener in accordance with claim 6 wherein the volatile compound is selected from the group consisting of a perfume, fragrance, scent and deodorant.

* * * * *